United States Patent [19]
Selesky et al.

[11] Patent Number: 5,890,181
[45] Date of Patent: Mar. 30, 1999

[54] SYSTEM AND METHOD FOR REMOTELY GROUPING CONTENTS OF AN ACTION HISTORY STACK

[75] Inventors: Donald Bryant Selesky, Westford; John Armstrong, Cambridge, both of Mass.

[73] Assignee: Kurzweil Applied Intelligence, Inc., Waltham, Mass.

[21] Appl. No.: 749,180

[22] Filed: Nov. 14, 1996

[51] Int. Cl.$^6$ .................................................. G06F 17/21
[52] U.S. Cl. .......................................... 707/530; 707/515
[58] Field of Search ................................. 707/530, 515, 707/516, 531, 539, 540

[56] References Cited

U.S. PATENT DOCUMENTS

| | | | |
|---|---|---|---|
| 5,537,526 | 7/1996 | Anderson et al. | 707/515 |
| 5,574,905 | 11/1996 | deCarmo | 707/1 |
| 5,655,136 | 8/1997 | Morgan | 382/182 |
| 5,659,747 | 8/1997 | Nakajima | 395/651 |
| 5,692,184 | 11/1997 | Ardoin et al. | 707/103 |
| 5,717,939 | 2/1998 | Bricklin et al. | 707/503 |
| 5,757,372 | 5/1998 | Krause et al. | 345/348 |
| 5,761,689 | 6/1998 | Rayson et al. | 707/533 |
| 5,778,402 | 7/1998 | Gipson | 707/530 |
| 5,802,380 | 9/1998 | Bangs et al. | 395/682 |

FOREIGN PATENT DOCUMENTS

| | | |
|---|---|---|
| 0 570 147 A2 | 5/1993 | European Pat. Off. . |
| WO 94/15281 | 7/1994 | WIPO . |

OTHER PUBLICATIONS

Nagashima Hironobu, Patent Abstracts of Japan, "Text Managing and Restoring System", Nov. 11, 1992.

Alain Karsenty et al., The 13th International Conference on Distributed Computing Systems, "An Algorithm for Distributed Groupware Applications", May 25–28, 1993, pp. 195–202.

Primary Examiner—Stephen S. Hong
Attorney, Agent, or Firm—Bromberg & Sunstein LLP

[57] ABSTRACT

A system and method for remotely grouping contents of an action history stack running on a computer system. An action is performed in a first application which causes a beginning marker to be placed on the action history stack. One or more actions are performed in the first application. Each action performed is also stored on the action history stack. Finally an action is performed which causes an end marker to be placed on the action history stack. When some actions need to be undone, a first action is caused to be undone. If the undone action indicates an end marker, then more actions are caused to be undone until an undone action indicates a beginning marker. This method is useful for any application which uses an action history stack, and where access to the action history stack is limited. In one embodiment, the application is a word processing program, and the steps of the invention are performed by a voice recognition system.

21 Claims, 5 Drawing Sheets

(PRIOR ART)

SYSTEM AND METHOD FOR REMOTELY GROUPING CONTENTS OF AN ACTION HISTORY STACK

BACKGROUND

As the number of applications for computer systems increases, so does the power and ease of use of such applications. One feature which many systems and applications now include as a standard attribute is an undo feature. This undo feature will "undo" the last action performed by a user of the system. In effect, the application returns to the state of the application just before the user performed the last action.

More sophisticated applications allow users to undo several or all previous actions. For example, in a word processing program, a user could sequentially delete several lines of text, and then go back and undo the deletions, thereby re-inserting each line of deleted text. In a spreadsheet application, a user could change the formulas attached to various cells, but then decide to convert those cells back to their original formulas.

A user gains much more freedom and control over their work from the ability to easily undo previous actions. Users can experiment with different styles or appearances, and undo or redo any features they want. Further, it is human nature to make mistakes. An undo feature allows most mistakes to be easily amended, requiring much less time than manually taking the steps to revert an application to its previous state.

Most applications which allow users to undo several steps implement this feature by storing each user action on an action history stack. Although the action history stack may not be visible to a user, any implementation of a multiple undo feature will include some variation of a stack.

When the application starts up, the action history stack is empty. Each action performed by a user, for example entering some text, highlighting a block of text, or moving to a different part of a document, is stored on the action history stack. When a user wishes to undo one or more previous actions, the user activates the undo feature. Many applications allow the user to perform one or several undo actions at a time. Each undo action causes the last entry on the action history stack to be undone. The action is popped off the action history stack. When the user performs more actions, these new actions are pushed onto the action history stack.

One problem with undo actions is defining what is a single action. For example in a word processing application, each keystroke can be considered an action. However, undoing each keystroke would require a user to undo a vast number of actions to simply delete a couple of words. Therefore many word processors group various actions into a single action to be undone. For example, most word processors treat a group of keystrokes as one action which becomes the action of inserting text. This one action is pushed onto the action history stack. The user is stuck with the option of undoing the whole insertion of text, not just any portion of the keystrokes. Therefore, the user is confined with the application's description of what an undo action is.

This becomes even more problematical when a second application tries to drive the first application with the action history stack. For example, if the second application is sending actions to the first application to perform, the first application is storing actions on its action history stack. If the second application then needs to undo some actions, it must know exactly how the first application stores actions on the action history stack. Otherwise the second application will not be able to determine if it has undone the correct number or type of actions.

This situation is even worse if the second application is not the only source of actions to the first application. For example, suppose the first application is a word processing program and the second application is a voice recognition system. The voice recognition system interprets a human user's voice and inputs the spoken words to the word processing program. The user both dictates words to be typed into the word processing program, and commands for manipulating the displayed text in various ways. As the user dictates, she is also entering text or commands using the keyboard. Therefore actions are inserted onto the action history stack from two sources, the keyboard and the voice recognition system.

If the voice recognition system needs to undo several actions it performed, it cannot determine which actions were performed by the voice recognition system, and which were inserted by the keyboard. Further, the voice recognition system may want to group a set of actions as one action, in a different grouping than imposed by the word processing application. Since the voice recognition system has no control over what the word processor puts on the action history stack, the voice recognition system cannot undo actions in a reasonable way.

Accordingly, what is required is a system and method for allowing an application to monitor what is placed on an action history stack of another application, and thereby maintain some control as actions are pushed onto and popped off the action history stack.

SUMMARY

This invention features a system and method for remotely grouping and tracking the contents of an action or command history stack. On a computer system which is running at least one application with an action history stack, a method for remotely grouping includes causing a beginning marker to be inserted on to the action history stack. Then zero, one, or more actions are performed in the application. The next step is causing an end marker to be inserted on to the action history stack.

The step of causing a beginning marker to be inserted on the action history stack is performed by causing at least one action in the application. This one action includes performing a first sub-action in the application, and then performing a second sub-action, which undoes the effects caused by the first sub-action. The step of causing an end marker to be inserted on the action history stack is similar. Preferably, these actions are not observable by a user observing the application.

The method further includes the steps of undoing actions in the application utilizing the beginning and end markers on the action history stack. One action is caused to be undone in the application. If the undone action indicates an end marker, then more actions are caused to be undone until an undone action indicates a beginning marker. Therefore, the present invention allows monitoring and recognition of actions placed on the action history stack, even though direct access to the action history stack is not possible.

In one embodiment, the application with the action history stack is a word processing program. The actions which cause the insertion of beginning and end markers are the insertion of elements into a document being processed by the word processing program. One such element is a bookmark, as used in Microsoft Word.

The methods utilized by the invention can be performed by a second application running on the same computer system as the fist application, or alternatively on a separate computer system. One such second application is a voice recognition program. The voice recognition system communicates with the first application using one of several methods including OLE (Object Linking and Embedding). The voice recognition system causes actions to be performed in the first application, which cause the actions to be placed on the action history stack. The voice recognition system then undoes these actions. These actions result in identifiable markers being placed on the action history stack. In between these actions, the voice recognition system performs actions and functions in the first application.

When the voice recognition system needs to undo actions in the first application, it causes actions to be undone, and detects whether an indication of an end or beginning marker was removed from the action history stack as a result of undoing one or more actions.

DETAILED DESCRIPTION

Figure 1:
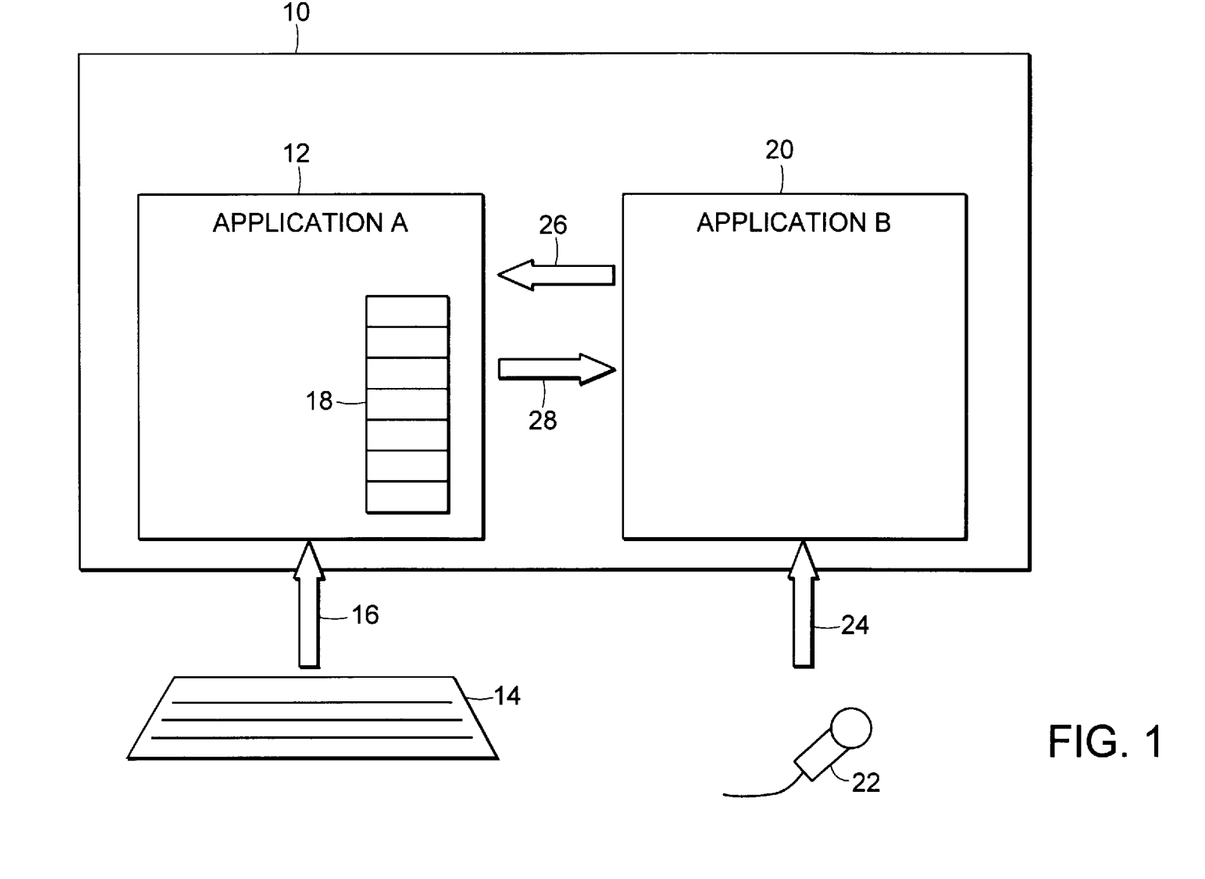
FIG. 1 is a general overview of a computer system including two computer applications, one of which is utilizing an action history stack.

Referring to FIG. 1, and overview of a computer system is shown. The computer system 10 can be any computer capable of performing sequential program execution, including personal computers, minicomputers, mainframes or portable personal digital assistants. The computer system 10 is running at least one application 12, referred to here as Application A. As used herein, an application is defined as a program or executable set of instructions running on a computer system, including operating systems, device independent programs, device drivers, user interfaces, word processors, spreadsheets, batch programs, and simulators.

Application A accepts user input 16 for example, by keyboard 14 and/or a mouse pointing device 15. As the user types in actions in the form of data and commands, Application A 12 performs those actions.

Application A 12 also stores the actions performed on action history stack 18. The storing of each action on action history stack 18 is usually invisible to the user. The user is simply aware that at any point, the user can undo one or more previous actions by instructing Application A 12 to do so.

Computer system 10 is also running another application 20, referred to here as Application B. Application B 20 is also providing input to Application A 12, as shown by arrow 26. There are many different techniques by which Application B 20 can provide input to Application A 12. They include mimicking input from a keyboard such as keyboard 14, interprocess communication, dynamic data exchange, cut and paste buffers, object linking and embedding, and other techniques.

Application B 20 is a completely separate application, possibly running on a separate computer system (not shown). In that case, Application B would provide input 26 to Application A 12 over a network system including RS-232, LAN, WAN, token ring or fiber optic. Alternatively, Application B 20 is a DLL (Dynamic Link Library) linked to or used by Application A 12, or a subroutine, library, or class. The system and method of the present invention works in any situation where Application A 12 does not allow or supply direct access to its internal mechanisms, including its action history stack 18.

For example, Application B 20 is a voice recognition system, receiving input 24 from a microphone device 22. Application B 20 performs analysis and conversion of audio signals into a format that is useable by Application A 12. In this example, if Application A 12 is a word processing program, Application B 20 would be providing character strings for insertion into a document. Application B 20 could also be providing commands to manipulate the document, such as changing fonts, moving text sections around, saving documents to long term storage etc.

Application A 12 may or may not be aware of the multiple input sources. However, Application A 12 performs actions based on the data it receives in the order it receives them. If Application A 12 is receiving input intermixed from the keyboard 16 and Application B 20, the actions Application A 12 is performing will be intermixed. The actions which are pushed onto action history stack 18 will also be intermixed.

Application B 20 often can determine some information about the state of Application A 12, as shown by arrow 28. This information can be obtained through direct querying of Application A 12 by Application B 20, or by other means of monitoring Application A 12. But what Application B 20 cannot determine is the contents of the action history stack 18 in Application A 12. Since Application A 12 is receiving input from more than one source, Application B 20 cannot know what intervening actions have taken place, which affect the contents of action history stack 18.

Continuing with the above example, if a user is adding information by keyboard 14 as well as providing voice commands to Application B 20, for manipulating the text in word processing Application A 12, the undo feature of Application A 12 will not distinguish between keyboard 14 actions, or voice 24 actions. If Application B 20 is instructed to undo a previous action or actions, Application B 20 is unable to determine which previous actions were implemented by it, and which previous actions came from another source.

This is even more problematic in the field of voice recognition, wherein a single voice command can result in several distinct word processing steps. As an example, the user command "Underline the Last Sentence" would require Application B 20 to inform Application A 12 to first find the last sentence, select the last sentence, underline the text, and return to the previous input location in the document. If the user then decides to undo that action, Application B 20 must know how to undo enough actions on the action history stack 18 to return the document on word processing Application A to its previous state (before the sentence was underlined).

Figure 2:
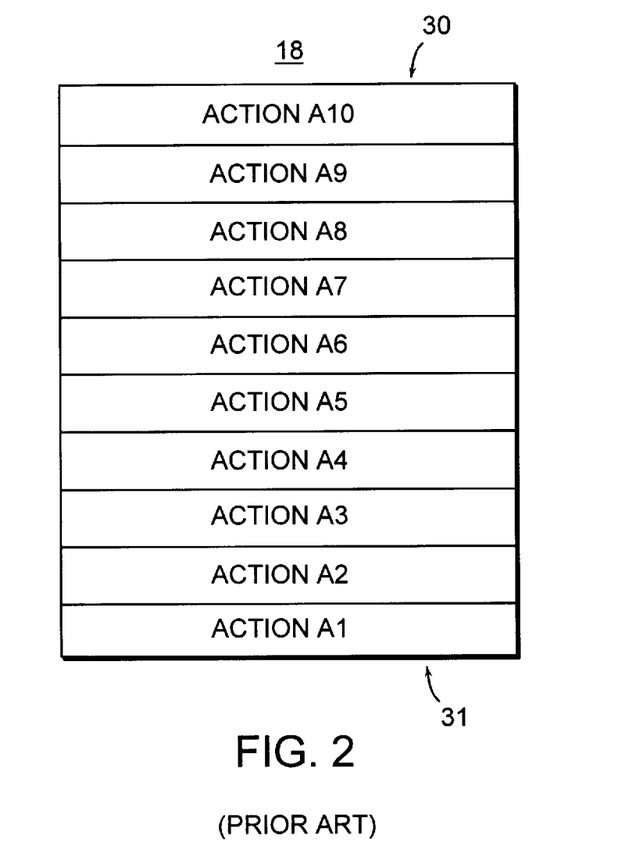
FIG. 2 is a view of an example action history stack.

An action history stack 18 FIG. 2 is a stack data structure as is well known in computer science. It has a "top" 30 which information is stored, and then retrieved in a LIFO (Last In, First Out) order. It also has a "bottom" 31, which is reached when all entries on the stack have been removed. In the case of an action history stack 18, the information stored on the stack is a description of each action performed by an application in response to user (or another application's) input. Each action is stored sequentially on the action history stack 18. To undo an action, the last action stored on the stack is popped off the stack, and the application takes whatever measures are required to undo the action. Note that the steps required to undo an action are often very complicated, depending on the application. Many applications allow users to undo several actions at once, by selecting more than one undo action as presented to the user.

The internal implementation of action history stack 18 in Application A 12 is not important. Although a stack is a well-known data structure abstraction, there are many different schemes for implementing a stack. For this application, a stack is defined as any data storage mechanism which can store and retrieve information in a Last In First Out (LIFO) fashion.

Since the action history stack 18 is an internal data structure to the application (Application A 12 for example), the action history stack 18 is not available to be examined and manipulated by other applications. Therefore other applications can only utilize the action history stack 18 by interfacing with Application A, through whatever means Application A allows access to the undo feature implemented by the action history stack 18.

Figure 3:
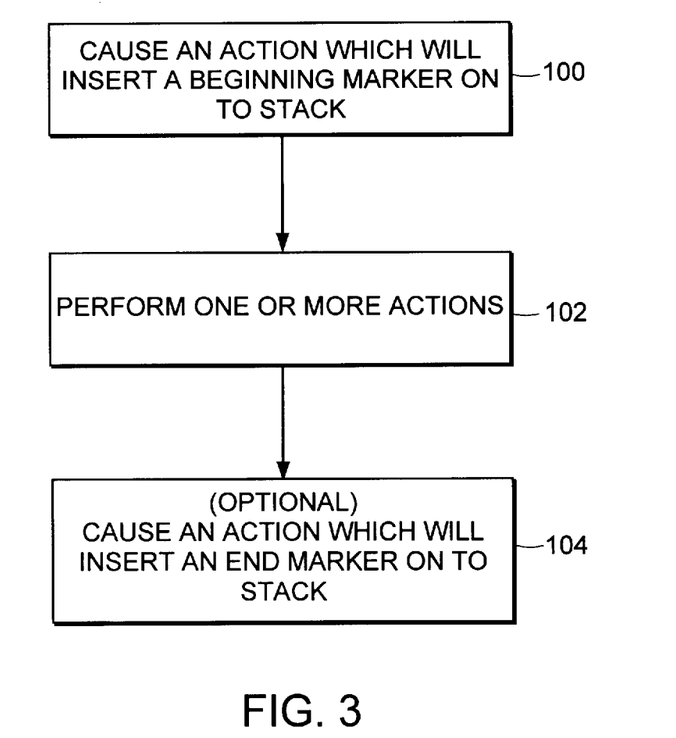
FIG. 3 is a flowchart showing the general steps performed in putting instructions on an action history stack, according to the present invention.

The general steps according to the present invention for assisting a computer system running an application, such as Application B 20, are shown in FIG. 3. At step 100, Application B 20 sends an action to Application A 12 which results in a beginning marker being placed on the action history stack 18. A more detailed description of such actions and beginning markers is discussed below.

Application B then sends over one or more actions to by performed by Application A, step 102. The performance of each of these actions results in the actions (or a description of the actions performed) to be stored on the action history stack 18.

When Application B 20 has finished in sending over the sequence of actions for Application A 12 to perform, Application B 20 then sends an action to Application A 12 which results in an end marker being placed on the action history stack 18.

Preferably, Application B should complete all steps without Application A performing any intermediate actions. Depending on Application A, Application B might perform the steps in a critical section. Therefore Application A will not perform any actions, or accept any input from any other sources until Application B finishes all the steps. In a secure multiprocessing environment with proper locking mechanisms, this should not be a problem.

Although FIG. 3 includes the step 104 of causing an action which will insert an end marker on to the stack, this step is not necessary. In certain situations, Application B 20 need only be able to recognize the end of the sequence of actions it has sent to Application A. One such example is when Application A is receiving input and commands only from Application B. Therefore the action history stack 18 will only contain actions caused by Application B. Application B would still need to recognize a group of actions sent by it as one action, but would not need to differentiate its actions from another source. In such a case, the beginning markers will delimit each group of Application B's actions. End markers would not be needed.

Figure 4:
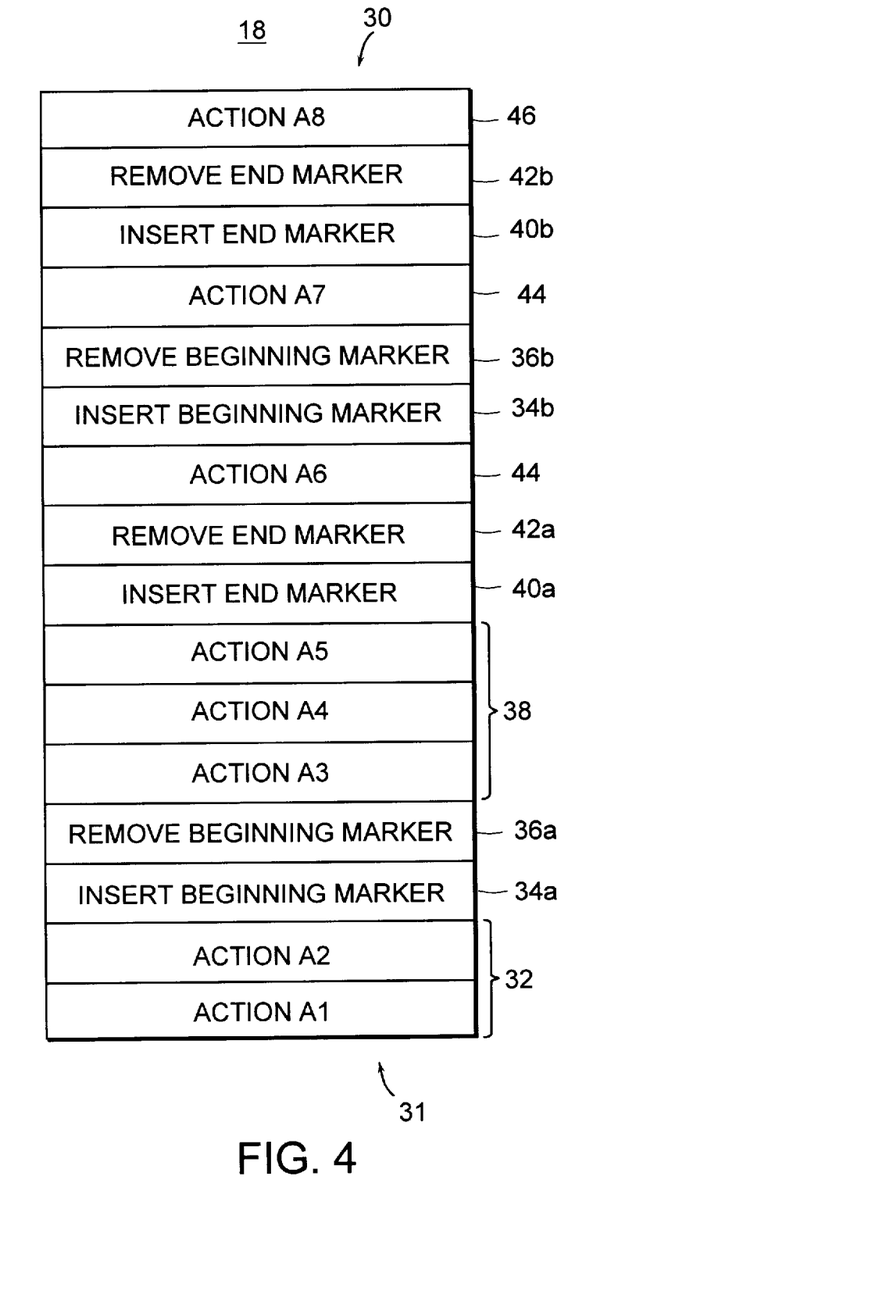
FIG. 4 is a view of an action history stack as manipulated according to the present invention.

One embodiment for manipulating an action history stack 18 according to the present invention is demonstrated in FIG. 4. Markers are placed in the action history stack 18 to delimit the beginning and end of sets of actions performed by an application such as Application B 20. Starting from the bottom 31 of action history stack 18, two action A1 and A2 32 are already on action history stack 18. If Application B 20 is starting to send a sequence of actions to Application A 12, Application B first sends over an action which causes an identifiable beginning marker 34*a* to be placed on action history stack 18.

The action which causes beginning marker 34*a* to be placed on action history stack 18 can be one of a wide range of actions. The only requirements are that Application B 20 can recognize beginning marker 34*a* when the action is undone. Also preferably the action should be invisible to a user who is observing and using the computer system. Any action which can be discerned by Application B 20 as an indication of the beginning of a set of actions would work. Some examples of possible beginning markers are insertion of invisible text in a word processor document, or selecting a range of cells in a spreadsheet application. In a preferred embodiment, which will be discussed below, the action includes insertion of a bookmark into a word processor document. The bookmark is invisible to a user, and includes a unique name, which is used as an identification for a location within the document on the word processor.

Once the action which inserted the beginning marker 34*a* onto action history stack 18 has been performed, Application B 20 then sends over an action which undoes the previous action. Note that the previous action is undone by a new action, not by using the undo feature of Application A 12. Therefore, the new action also gets stored on action history stack 18 as a removal of a beginning marker 36*a*.

Now Application B sends over one or more actions 38, which perform functions in Application A 12, and are stored on action history stack 18. At the completion of the actions, Application B 20 causes an action which will insert an end marker 40*a* on action history stack 18. This action which causes an end marker 40A is similar to the action which caused beginning marker 34*a* to be inserted.

In the preferred embodiment, the actions should be different: to be distinguishable in that Application B can detect the difference between an action which signals a beginning marker 34*a* and an action which signals an end marker 40*a*. This avoids a situation where if a marker serving as an end marker gets removed from the action history stack 18, Application B 20 might confuse actions from another input source as its own. In other words, if end marker 40*a* gets removed, Application B 20 could reasonably expect actions A3–A5 38 to be actions caused by another input source, and undo those actions in an improper fashion. Using an end marker which is distinguishable from a beginning marker avoids this problem. Even if the action history stack 18 gets corrupted, Application B 20 will be able to recover and recognize its actions on the action history stack 18.

Application B then sends over an action which undoes the previous action, and which results in a removal end marker 42*a* being placed on action history stack 18.

An action A6 44, has then been placed on action history stack 18 by some input to Application A 12 other then from Application B 20. For example, the user may have typed some input from a keyboard 14.

Continuing with the action history stack 18 as shown in FIG. 4, Application B 20 has sent over another action, action A7 44. Even though it is a single action, it too is prefaced by two beginning actions, which cause a beginning marker to be inserted 34*b* and removed 36*b*; and followed by two end actions, which cause an end marker to be inserted 40*b* and removed 42*b*.

Although the actions 34, 36 which cause the beginning marker to be inserted are identical for each set of actions, the actions 34*a* and 34*b*, 36*a* and 36*b* don't have to be identical. Application B can use a different beginning marker for each set of actions it sends over. The actions 34, 36 could generate a unique beginning marker. Application B could easily generate a unique marker or even an incrementing serial number, to mark the beginning of each sequence of actions. In this way, Application B can keep track of the total number of action sets it has sent to Application A. The end marker actions 40, 42 also can be all different.

Finally, as shown in FIG. 4, a last action A8 46 was performed by a source other than Application B.

Figure 5:
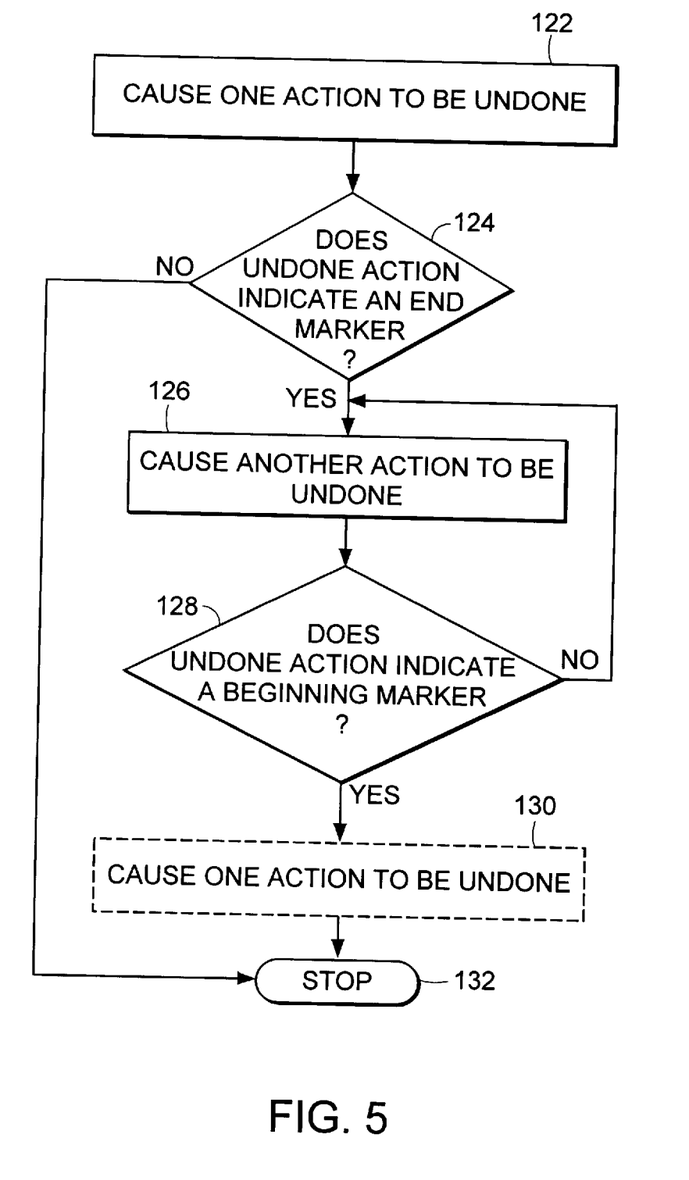
FIG. 5 is a flowchart showing the steps performed in reading instructions off an action history stack, according to the present invention.

The steps performed in undoing an action are shown in FIG. 5. Application B 20 requires a last action to be undone, either through internal login, or in response to a user request to undo a last action. Application B 20 instructs Application A 12 to undo one action, step 122.

Application B then determines if the undone action indicates an identifiable end marker 42 FIG. 4, step 124 FIG. 5. In determining this, Application B 20 queries Application A whether a certain marker is present in application. For example, in a word processing application, the undone action would cause the insertion of a bookmark into the document. Application B 20 would query Application A 12 as to whether a certain bookmark was present in the document. If the bookmark was present, that indicates to Application B 20 that the action history stack 18 contained an end marker 42*b*. Application B 20 could also use any number of techniques to determine whether the undone action indicates an end marker, including analysis of the state of Application A 12, and interpretation of displayed states of Application A 12 by screen capture.

If in step 124 it is determined that the undone action does not indicate an end marker, then Application B 20 stops, step 132. Since the action that was just undone was not originally caused by Application B 20, Application B 20 proceeds no further. If a user wishes to have more actions undone, the user will indicate to Application B to undo another action, or indicate to Application A to undo an action in another way, possibly by keyboard 14 or a mouse/menu interface (not shown).

If in step 124 it is determined that the undone action does indicate an end marker, then Application B instructs Application A to undo another action, step 126.

In step 128, Application B then determines if the undone action indicates an identifiable beginning marker 36 FIG. 4. The analysis and determination are similar to as previously discussed. If an identifiable beginning marker is not detected, then another action is undone, step 126, and checked, step 128. This continues until a beginning marker is detected at step 128.

Application B 20 now can determine that it has undone all the actions it has caused in Application A 12. Application B 20 therefore has greater control over the actions it causes in Application A 12, including the ability to group its actions in a different way than enforced by Application A for storing on the action history stack 18.

In the last step 130 as needed for the preferred embodiment, Application B 20 causes one more action to be undone. This then removes the indication used to cause a beginning marker 34 to be inserted on action history stack 18.

An application which incorporates the present invention is a voice recognition system produced by Kurzweil Applied Intelligence of Waltham, Mass. In one embodiment, the voice recognition system runs on a personal computer running Microsoft Windows(TM) NT. The voice recognition system interfaces with another running application, such as a word processing program such as Microsoft Word(TM). A user, using an input device such as a microphone or headset, can speak words or commands. The audio signal is converted into digital data using a plug in A/D sound card, which are widely available. One producer of such sound cards is SOUNDBLASTER(TM) inc.

The voice recognition system preferably communicates with Microsoft Word using OLE (Object Linking and Embedding). Other methods of communicating between the applications include DDE (Dynamic Data Exchange), and keyboard simulation.

Microsoft Word version 6.0 includes an undo feature which allows a user to undo one or multiple actions at a time. A pull-down menu show a list of the previous actions, allowing a user to select how many actions to undo. A redo feature is also available, allowing a user to redo all or part of the previously undone actions.

In a preferred embodiment of the present invention, the voice recognition system uses Microsoft Word bookmarks to cause actions that place beginning markers and end markers on the action history stack. Code written in Microsoft WordBasic is shown in Appendix A, which implements this feature.

When the voice recognition system is about to send input to Microsoft Word, a bookmark with the name "KVWin_undostart" is inserted into the document. The name chosen is arbitrary, the only requirement is that the name be different from the name used for an ending bookmark. Bookmarks are invisible to users. Where the bookmark is inserted into the document is not important. Other word processing programs have features similar to bookmarks, although the term "bookmark" might not be used. For another word processing program, a feature similar to the functionality of a Microsoft Word bookmark would be employed.

Immediately after inserting the bookmark, it is removed. This leaves the document unchanged, but the insertion and deletion of the bookmark are recorded on the action history stack.

After the voice recognition system performs actions on the document in Microsoft Word, a bookmark with the name "KVWin_undo end" is inserted into the document, and then removed. Once again, these actions are recorded on the action history stack.

When the voice recognition system wishes to undo an action, first one action is undone. Then the document is checked to see if the bookmark "KVWin_doend" is present. Microsoft Word includes a function which allows a user or application to check for the presence of a bookmark, without jumping to the bookmark if it exists.

If the bookmark does not exists, then no other action is performed. However, if the bookmark is present, then a loop is entered whereby actions are undone, and the document is checked for the presence of the bookmark "KVWin_dobegin". When the bookmark suddenly appears in the document, this signals that the set of actions performed by the voice recognition system (which are now being undone) is now complete. One more undo action is performed to remove the "KVWin_dobegin" bookmark (thereby undoing its insertion in the document).

While actions are being undone, the screen display updating of Microsoft Word can be turned off, if necessary, to avoid the document appearing "jumpy" while the actions are undone.

This invention also works for redoing actions, using the redo feature as available in Microsoft Word. As shown in Appendix A, the redo implementation is similar to the undo implementation, except that the beginning marker, "KVWin_dobegin" is checked for first, followed by a loop that redoes actions, and checks for the end marker, "KVWin_doend". This functions correctly in that as Microsoft Word stores undone commands on a "redo stack", allowing a user to redo one or all of the undone commands. Since the actions are sequentially popped off the action history stack and pushed onto the redo stack, the order of the markers ("KVWin_dobegin" and "KVWin_doend") are in reverse order on the redo stack. The present invention allows any combination of undos and redos, and will function correctly in all circumstances.

Further, there can be more than one application using this feature while sending actions to the one application with an action history stack. In effect, each application has grouped its actions as a set, and any one application can undo actions of its own or another. In each case, the set of actions will be treated as one undo action.

Should a user undo an action using the keyboard 14, and thereby remove an end marker from action history stack 18, the computer system and applications are still useable. Application B 20, upon instruction to undo an action, will simply undo one action instead of a group of actions. The user can then instruct Application B 20 to undo more actions, or perform the undo operations using the keyboard 14. The steps of the invention guarantee that a beginning marker will always be proceeded by an end marker, without another beginning marker in between. Therefore, if the action history stack 18 should lose an end marker, Application B will never undo more actions than it should, it will only undo less actions.

Accordingly, this invention allows remote tracking and grouping of the contents of an action history stack. An application can readily identify which actions were performed by it, and undo those actions as a group, or individually.

As various changes could be made in the above constructions without departing from the scope of the invention, it should be understood that all matter contained in the above description or shown in the accompanying drawings shall be interpreted as illustrative and n in a limiting sense.

Appendix A sub markundostart
    WB.EditBookmark Name:="KVWin_dostart", Add:=1
    WB.EditBookmark Name:="KVWin_dostart", Delete:=1
end sub
sub markundoend
    WB.EditBookmark Name:="KVWin_doend", Add:=1
    WB.EditBookmark Name:="KVWin_doend", Delete:=1
end sub
sub cmdundo
    wb.editundo
    if wb.existingbookmark ("KVWin_doend") then
        while not wb.existingbookmark ("KVWin_undostart")
            wb.editundo
        wend
        wb.editundo
    end if
end sub
sub cmdredo
    wb.editredo
    if wb.existingbookmark ("KVWin_dostart") then
        while not wb.existingbookmark ("KVWin_doend")
            wb.editredo
        wend
        wb.editredo
    end if
end sub

We claim:

1. A method for a computer control process to direct a computer subject process having an action history stack that is not directly observable by the control process, the method comprising:

a. causing the history stack to record a beginning marker by directing the subject process to perform a beginning marking action having an effect that is directly observable by the control process, then     b. directing the subject process to perform a desired action which is recorded by the bistory stack as a grouped set of subject process action entries, the number of entries in the set being not directly observable by the control process; and then     c. causing the history stack to record an ending marker by directing the subject process to perform an ending marldng action having an effect that is directly observable by the control process;

so that when the control process causes undoing of the desired action, the appearance of the effect of the beginning marking action signals to the control process that the desired action has been undone.

2. A method as in claim 1, wherein the control process is an automatic speech recognition process.

3. A method as in claim 1, wherein the subject process is a word processing process.

4. A method as in claim 1, wherein the subject process is a spreadsheet process.

5. A method as in claim 1, wherein the step of causing the history stack to record a marker includes:

directing the subject process to perform a first action having an effect that is directly observable by the control process and that the history stack records, and then     ii. directing the subject process to perform a second action that the history stack records and that undoes the fist action.

6. A method as in claim 5, wherein the marker is the beginning marker.

7. A method as in claim 5, wherein the marker is the ending marker.

8. A method as in claim 5, wherein the first action is insertion of a bookmark.

9. A method as in claim 8, wherein the second action is deletion of the bookmark.

10. A method as in claim 5, wherein the first action is selecting a range of spreadsheet cells.

11. A method as in claim 10, wherein the second action is deselecting the range of spreadsheet cells.

12. A method as in claim 1, wherein the undoing of the desired action includes:

i. causing the subject process to -undo the last action in the history stack, and     ii. if the control process observes that the subject process has the begining marker as the last entry in the history stack,         (1) causing the subject process to undo the last action in the history stack, and otherwise         (2) repeating steps (i) and (ii).

13. A method as in claim 12, wherein before step (i), undoing the desired action further includes causing the subject process to undo the last action in the history stack, and if the control process observes that the subject process has the ending marker as the last entry in the history stack, continuing to steps (i) and (ii).

14. A method for a computer control process to direct a computer subject process having an action history stack that is not directly observable by the control process, the method comprising:
   a. directing the subject process to perform a first action having an effect that is directly observable by the control process and that the history stack records; and then
   b. directing the subject process to perform a second action that the history stack records and that undoes the first action;
      so that under a circumstance, (i) after a desired action has been recorded by the history stack as a grouped set of subject process action entries, the number of entries in the set being not directly observable by the control process, and (ii) when the control process causes undoing of the desired action, the appearance of the effect of the first action signals to the control process that the desired action has been undone.

15. A method as in claim 14, wherein the control process is an automatic speech recognition process.

16. A method as in claim 14, wherein the subject process is a word processing process.

17. A method as in claim 14, wherein the subject process is a spreadsheet process.

18. A method as in claim 14, wherein the first action is the insertion of a bookmark.

19. A method as in claim 18, wherein the second action is deletion of the bookmark.

20. A method as in claim 14, wherein the first action is selecting a range of spreadsheet cells.

21. A method as in claim 20, wherein the second action is deselecting the range of spreadsheet cells.

* * * * *

UNITED STATES PATENT AND TRADEMARK OFFICE
CERTIFICATE OF CORRECTION

PATENT NO. : 5,890,181

DATED : March 30, 1999

INVENTOR(S) : Selesky, et al

It is certified that error appears in the above-indentified patent and that said Letters Patent is hereby corrected as shown below:

On the title page, change Assignee from "Kurzwell" to "Kurzweil"

Column 9, line 43, change "n" to "not"

Colum 10, line 17, change "bistory" to "history"

Column 10, line 23, change "marldng" to "marking"

Column 10, line 43, change "fist" to "first"

Column 10, line 58, remove the hyphen (-) before the word undo

Column 11, line 16, change the comma (,) after the word circumstance to a colon (:)

UNITED STATES PATENT AND TRADEMARK OFFICE
CERTIFICATE OF CORRECTION

PATENT NO. : 5,890,181
DATED : March 30, 1999
INVENTOR(S) : Selesky, et al

It is certified that error appears in the above-indentified patent and that said Letters Patent is hereby corrected as shown below:

Column 3, line 35, change "and" to "an"

Column 5, line 67, change two "action" to "actions"

Column 8, line 16, change "show" to "shows"

Column 8, line 52, change "exists" to "exist"

Signed and Sealed this

Twenty-eighth Day of September, 1999

Q. TODD DICKINSON

*Attest:*

*Attesting Officer*      *Acting Commissioner of Patents and Trademarks*